United States Patent
Hermann et al.

(10) Patent No.: US 6,749,361 B2
(45) Date of Patent: Jun. 15, 2004

(54) SHACKLE ELEMENT FOR CLAMPING A FIXATION ROD, A METHOD FOR MAKING A SHACKLE ELEMENT, A HOOK WITH A SHACKLE ELEMENT AND A RODE CONNECTOR WITH A SHACKLE ELEMENT

(75) Inventors: Werner Hermann, Keltenweg 6, CH-6312 Steinhausen (CH); Klaus A. Matzen, Augsburg-Goeggingen (DE); Beat Buetler, Huenenberg (CH)

(73) Assignee: Werner Hermann, Steinhausen (CH)

( * ) Notice: Subject to any disclaimer, the term of this patent is extended or adjusted under 35 U.S.C. 154(b) by 164 days.

(21) Appl. No.: 09/784,322

(22) Filed: Feb. 16, 2001

(65) Prior Publication Data

US 2001/0020168 A1 Sep. 6, 2001

Related U.S. Application Data

(63) Continuation-in-part of application No. 09/163,206, filed on Sep. 30, 1998, now abandoned.

(30) Foreign Application Priority Data

Oct. 6, 1997 (CH) .............................................. 2333/97

(51) Int. Cl.$^7$ ............................................... A61B 17/70
(52) U.S. Cl. ........................ 403/399; 403/400; 606/60; 606/61; 248/230.6
(58) Field of Search ................................ 403/399, 400; 606/61, 60; 248/230.6, 121

(56) References Cited

U.S. PATENT DOCUMENTS

| | | |
|---|---|---|
| 2,088,890 A | 8/1937 | Winby et al. |
| 4,483,334 A | 11/1984 | Murray |
| 4,641,636 A | 2/1987 | Cotrel |
| 4,815,453 A | 3/1989 | Cotrel |

(List continued on next page.)

FOREIGN PATENT DOCUMENTS

| | | |
|---|---|---|
| DE | 3924050 A1 | 1/1991 |
| EP | 0 536 066 A1 | 4/1993 |
| EP | 0 540 317 A1 | 5/1993 |
| EP | 0 553 424 A1 | 8/1993 |
| WO | WO 95/28889 A1 | 11/1995 |
| WO | WO 98/44859 A1 | 10/1998 |

*Primary Examiner*—Anthony Knight
*Assistant Examiner*—Ernesto Garcia
(74) *Attorney, Agent, or Firm*—Browdy and Neimark, P.L.L.C.

(57) ABSTRACT

A shackle element, a method of making a shackle element, a hook and a rod connector. The shackle element (18) is used for fastening a hook (12), or respectively a rod connector, on a fixation rod (10). The shackle element (18) forms a groove with a lateral opening for inserting the fixation rod (10). The groove is delimited by a groove bottom (18.1) and two lateral walls (18.2, 18.3). After mounting the groove bottom (18.1) encloses the fixation rod (10) over an angle of 180° plus a partial angle. The lateral walls are arranged under a small angle; their distance increases with growing distance from the groove bottom so that the lateral opening is large enough for introducing the rod. The lateral walls are intended to be pushed together by means of a screw device (20.1, 20.2) for clamping the fixation rod (10). The groove bottom (18.1) encloses the fixation rod (10) over an angle of 180° plus a partial angle. The hook (12) has the shackle element (18) and a hook element (16), which grips a laterally extending portion (1) of a spine of a patient underneath or from above. The rod connector (32) has the shackle element (18) and a clamping device (34) for a transverse rod (10.1), which is oriented transversely in respect to the fixation rod (10). The hook (12) and the rod connector (32), along with fixation rods (10) and transverse rods (10.1), are employed as parts of internal orthopedic fixation devices.

10 Claims, 4 Drawing Sheets

U.S. PATENT DOCUMENTS

| | | |
|---|---|---|
| 4,946,122 A | 8/1990 | Ramsey et al. |
| 5,010,879 A | 4/1991 | Moriya et al. |
| 5,084,049 A | 1/1992 | Asher et al. |
| 5,102,412 A | 4/1992 | Rogozinski |
| 5,222,954 A | 6/1993 | Baker et al. |
| 5,281,222 A | 1/1994 | Allard et al. |
| 5,380,325 A | 1/1995 | Lahille et al. |
| 5,437,671 A | 8/1995 | Lozier et al. |
| 5,482,235 A | 1/1996 | Atsumi |
| 5,507,746 A | 4/1996 | Lin |
| 5,540,689 A | 7/1996 | Sanders et al. |
| 5,613,968 A | 3/1997 | Lin |
| 5,676,665 A | 10/1997 | Bryan |
| 5,746,741 A | 5/1998 | Kraus et al. |
| 5,810,817 A | 9/1998 | Roussouly et al. |
| 5,947,965 A | 9/1999 | Bryan |
| 5,984,928 A | 11/1999 | Hermann |
| 5,989,251 A | 11/1999 | Nichols |

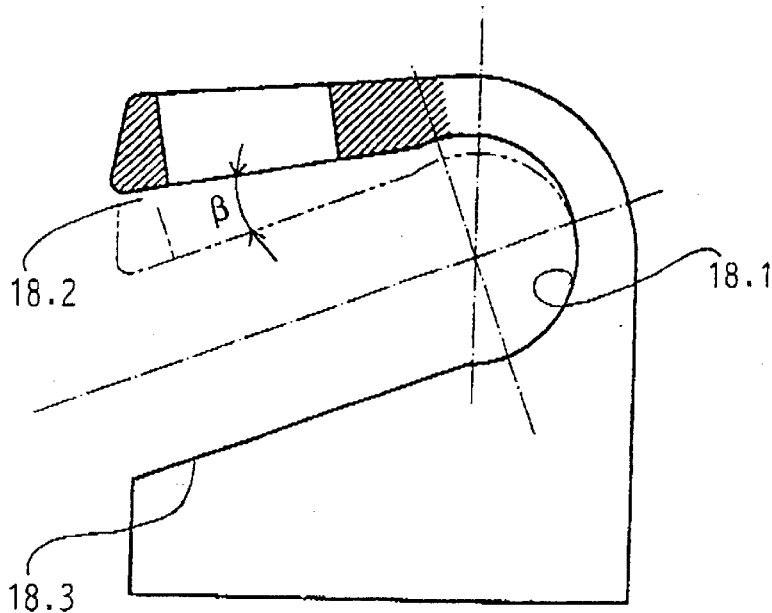
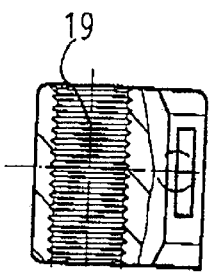
Fig. 2D
Fig. 2E
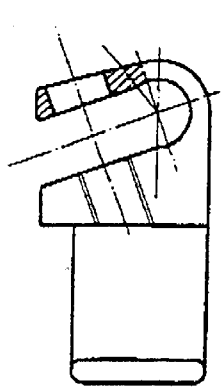
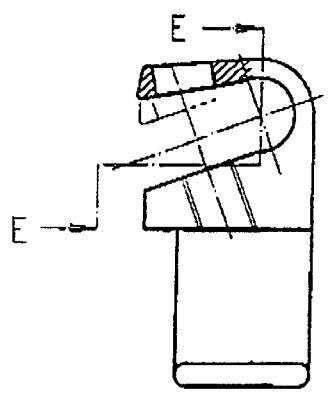
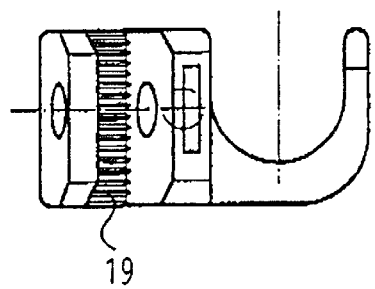
Fig. 2B
Fig. 2C
Fig. 2F
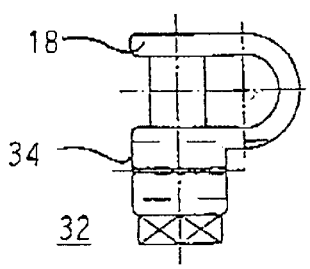
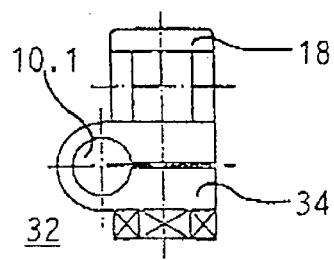
Fig. 3A
Fig. 3B

SHACKLE ELEMENT FOR CLAMPING A FIXATION ROD, A METHOD FOR MAKING A SHACKLE ELEMENT, A HOOK WITH A SHACKLE ELEMENT AND A RODE CONNECTOR WITH A SHACKLE ELEMENT

This application is a continuation-in-part of application Ser. No. 09/163,206, filed Sep. 30, 1998, entitled SHACKLE ELEMENT FOR CLAMPING A FIXATION ROD, HOOK WITH A SHACKLE ELEMENT, ROD CONNECTOR WITH A SHACKLE ELEMENT AND USE OF THE HOOK, OR RESPECTIVELY, THE ROD CONNECTOR, abandoned.

FIELD OF THE INVENTION

The invention relates to a shackle element, to a method for making a shackle element, a hook with a shackle element and a rode connector with a shackle element.

BACKGROUND OF THE INVENTION

Hooks and rod connectors are employed in orthopedic medicine for patients who, for example because of spondylosis, temporarily or permanently require an internal fixation device. Within the framework of the present specification, the term hook is intended to include all such hooks, for example pedicle hooks, lamina hooks, lumbar hooks and transversal hooks, wherein the latter are employed as safety hooks, for example for pedicle hooks. By means of internal fixation device it is attempted for the patient to be free of symptoms, even though it must be accepted that his mobility is restricted. In general, one fixation rod per side of the body and essentially extending in the direction of the spine is provided, wherein each fixation rod is equipped with at least two hooks. The two fixation rods are coupled with each other by approximately horizontally extending transverse rods, which are also identified as transverse connectors, wherein respectively one rod connector is used for the mutual connection of the fixation rod and transverse rod.

The hook has an actual hook element, which from the back grips a laterally extending portion of the spine from underneath or above, and a shackle element produced integrally with the hook element, which is used for receiving and fastening the fixation rod.

The rod connectors have a clamping device for fastening on the transverse rod, and a shackle element for clamping the fixation rod, wherein the clamping device for the transverse rod can be designed the same as or differently from the shackle element for the fixation rod.

The shackle element which is essentially designed the same for the hook and the rod connector, forms a groove extending in the direction of the fixation rod, having a groove bottom and two laterally connected lateral walls. When affixing the internal fixation device the process is such, for example, that the required hooks per body side are attached, then the fixation rod with the rod connectors is introduced laterally into the groove formed by the shackle element, thereafter the transverse rods are attached and fixed in place, and finally the hooks and rod connectors are definitely fixed in place on the fixation rod.

A perfect mutual connection between the hooks, or respectively the rod connectors, and the fixation rod is of decisive importance for the perfect functioning of such an internal fixation device. This connection cannot be permitted to become loose either by the effects of heat or by mechanical stresses, and the creation of abrasion particles must be prevented.

In connection with a known hook, the shackle element is designed in such a way that a screw is screwed into a lateral wall of the groove which is embodied to be flat, because of which the front of the screw bolt is pressed on the fixation rod, so that the fixation rod is squeezed, or respectively clamped, between the screw bolt and the opposite lateral wall. It is obvious that such fastening is unsatisfactory. On the one hand, the fixation rod can be displaced comparatively easily along the flat lateral wall transversely in respect to its longitudinal axis and, on the other hand, a very high pressure is exerted at the place of the practically only point-like contact between the screw bolt and the fixation rod, which favors the creation of abrasion particles.

In connection with another known hook, whose shackle element corresponds to that of the prior art mentioned at the outset, this shackle element forms a groove with a groove bottom which is semicircular in cross section and which continues on both sides into lateral walls which are parallel to each other. Here, too, fastening is provided by a screw acting on the surface of the fixation rod. The extension of the longitudinal axis of the screw does not lead radially through the respective cross section of the fixation rod, but in the direction of a secant of this cross section, namely in the area of the half of the cross section not in contact with the groove bottom. An improvement in comparison with the first described known hook is achieved, because a displacement of the fixation rod transversely to its longitudinal direction is prevented by means of the screw, which in respect to the fixation rod is eccentrically arranged. But, as already mentioned, in connection with this hook fastening of the fixation rod in the fastening element is also provided by means of a screw whose front is pressed directly on the fixation rod, which can lead to the creation of abrasion particles.

In summary, it can be stated that no shackle elements for hooks and rod connectors are known which are designed in such a way that a connection, which is perfect in every way, with the fixation rod is assured.

OBJECT AND SUMMARY OF THE INVENTION

It is therefore the object of the invention to improve the shackle element of the type mentioned at the outset in such a way that the mentioned disadvantages are avoided, propose a method for making the shackle element;

propose an improved hook and propose an improved rod connector.

These objects are attained in accordance with the invention by the features of the independent claims. Dependent claims define preferred embodiments of the shackle element, of the method for making the shackle element, and of the of the hook.

The novel shackle element is embodied in such a way that it forms a groove, whose groove bottom in cross section not only extends along an arc with an angle of 180° but also along an additional narrow partial angle, so that the fixation rod is enclosed by the groove bottom over more than half its circumference. When making the shackle element, the two lateral walls adjacent the groove in general are first parallel, whereby the distance between them is less than the diameter of the fixation rod. Then the walls are spread apart from each other, so that there is a small angle between them and their minimum distance at the place where they meet the groove is slightly larger than the diameter of the rod. This allows for easy transverse mounting of the rod. Then the clamping of the fixation rod in the shackle element by means of the screw device takes place by squeezing the two lateral walls of the groove again towards each other. As a result a displacement of the fixation rod transversely in respect to its axis is prevented by the novel shape of the groove, and the force exerted during the clamping of the fixation rod acts along a considerable surface, so that large point-like stresses which might lead to fissures are avoided.

As already mentioned the shackle element may be constructed such that the distance of the lateral walls from each other is slightly less than the diameter of the groove, or respectively of the fixation rod, so that the lateral walls directly follow the opening of the groove bottom. However, it would also be possible to select the distance of the lateral walls from each other corresponding to the diameter of the groove bottom, or respectively of the fixation rod, wherein the lateral walls then would start at a lesser distance from the opening of the groove bottom.

The screw device is preferably designed in such a way that the one of the lateral walls of the groove has an interior screw thread, and the other of the lateral walls of the groove has a through bore. For clamping the two lateral walls together, a cap screw or a screw bolt with a nut is screwed through the through bore into the interior screw thread.

Two requirements must be considered when determining the screw-in depth, or respectively the number of the screwed-in screw turns: on the one hand, the shackle element should have the lowest possible volume in order to minimize muscle problems for the patients, on the other hand, a certain screw-in depth must be provided in order to achieve a sufficient rigidity of the screw connection. It has therefore been found to be advantageous to design the lateral wall with the interior screw thread thicker in the direction of the longitudinal thread axis than the lateral wall provided with the through bore.

In order to secure the screw connection also without the use of an additional securing element, the exterior surface of the lateral wall provided with the through bore, against which the screw cap of the cap screw or the nut rest in the assembled state, can have one, or possibly several small protrusions, which are compressed when the screw connection is tightened and therefore exert a resilient counterpressure on the screw cap or the nut, so that the screw connection is secure against being loosened.

It was shown to be advantageous, in particular as an aid in assembly, to fix the distance of the longitudinal thread axis from the center of the circle, which can be drawn in the groove bottom, or respectively from the longitudinal axis of the fixation rod, in such a way, that it corresponds to the sum of the radii of the mentioned circle which can be drawn in, and of the screw bolt, the latter preferably being without threads in this area. Because of this the fixation rods acts as a guide for the screw while it is being screwed in, and in the assembled state the screw bolt rests against the fixation rod.

Besides a shackle element in accordance with the invention, the hook of the invention has an actual hook element, which is intended to extend underneath or over an essentially laterally extending portion of the spine of a patient.

In accordance with the use of the hook, the actual hook element is designed in such a way, that the hook is a pedicle, lamina, lumbar or transversal hook, and embodiments of all hooks which can be used on the right side as well as on the left side are produced in straight as well as in angled variants.

Besides a shackle element in accordance with the invention, the rod connector of the invention has a clamping device for a transverse rod.

The hook, or respectively the rod connector, is intended to be used, together with a fixation rod on which it is fastened by means of the screw device, as a portion of an internal orthopedic fixation device, wherein the lateral walls of the shackle element, whose distance from each other generally is slightly less than the diameter of the fixation rod, are spread apart by plastic deformation prior to inserting the fixation rod, preferably already when the hook is made Then, in the course of tightening the screw device, the lateral walls are elastically, and possible also plastically deformed.

For the purpose of preventing tension elements, all components of the internal fixation device, i.e. the hooks, the screw device and the fixation rod, are preferably made of the identical material, wherein titanium-niobium alloys have been shown to be particularly advantageous.

Further properties and advantages of the invention will be extensively described by means of exemplary embodiments, making reference to the drawings.

BRIEF DESCRIPTION OF THE DRAWINGS

FIG. 2B represents the hook of FIG. 2A, without the fixation screw and with lateral walls in parallel;

FIG. 2C represents the hook of FIGS. 2A and 2B ready for receiving the fixation rod with lateral walls spread apart from each other;

FIG. 2D represents a detail of FIGS. 2A to 2C in greater scale;

FIG. 2E represents a section along E—E of FIG. 2C;

FIG. 2F represents the hook of FIGS. 2A to 2E in a side view;

FIG. 3A represents a rod connector in a view from above;

FIG. 3B represents the rod connector represented in FIG. 3A in a view from the side;

DETAILED DESCRIPTION OF THE PREFERRED EMBODIMENTS

Figure 1:
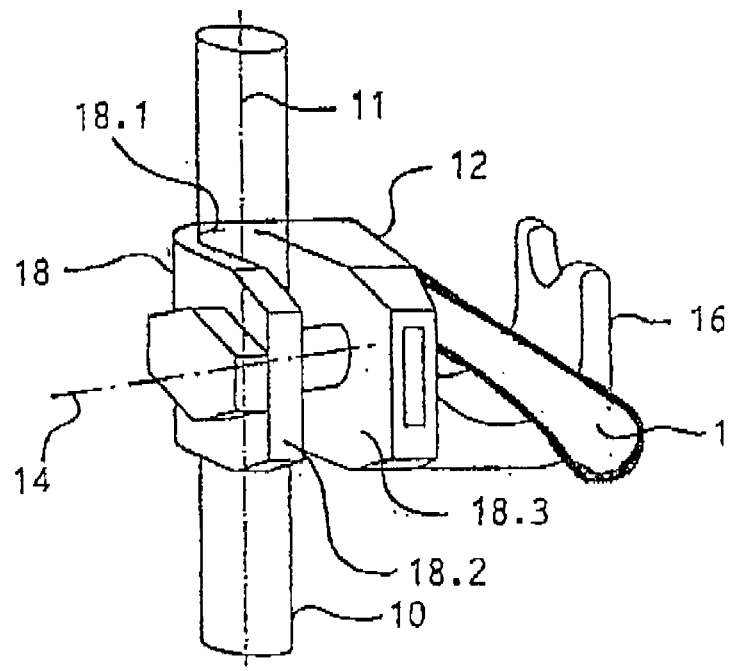
FIG. 1 represents a portion of an internal fixation device in accordance with the invention with a hook embodied as a pedicle hook.

FIG. 1 represents, greatly simplified, a laterally extending portion 1 of a spine of a human patient, with a section of an internal fixation device, comprising a fixation rod 10 and a hook 12 with a screw device with an axis 14. The hook 12 has an actual hook element 16 and a shackle element 18 which, in the present case, grips the portion 1 of the spine in FIG. 1 from below from the left to the right—viewed from the direction of the patient from the rear to the front—. The shackle element 18 is used to fasten the fixation rod 10 and the hook 12 on each other. The shackle element 18 forms a groove with a groove bottom 18.1, against which the fixation rod 10 rests, and two lateral walls 18.2, 18.3 following the groove bottom 18.1. The two lateral walls 18.2, 18.3 of the shackle element 18 are clamped together by means of the screw device having the axis 14, by means of which the fixation rod 10 is clamped in place with its area received in the shackle element 18. In the implanted state the hook 12 will take up a position in which its opening, through which the fixation rod 10 has been inserted, is laterally oriented, and viewed in FIG. 1, tightening of the screw device takes place from the left—viewed from the patient from the back—. Thus, the hook 12 represented in FIG. 1 is designed for use on the right side of the body and, as already mentioned, for gripping the portion 1 of the spine from below. The size and design of the hook are a function of the intended use and of the size of the body of the patient.

Figure 2A:
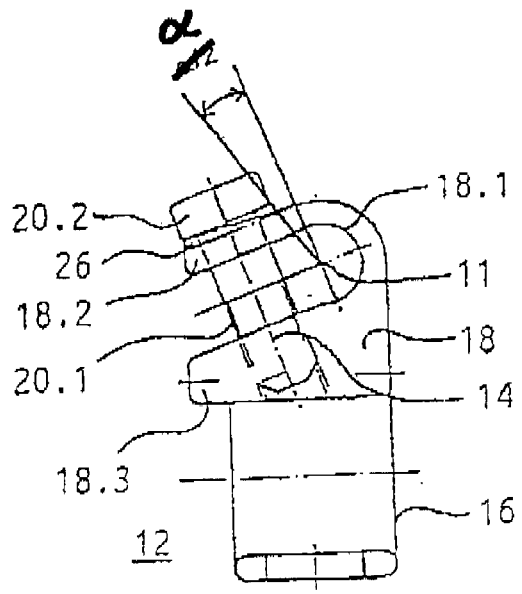
FIG. 2A represents a hook in accordance with the Invention with the fixation screw; seen from above.

A hook 12 with a shackle element is represented in FIGS. 2A to 2F; in FIGS. 2B to 2F most of the reference numerals are left away. The hook as represented in FIGS. 2A, 2B, 2C, 2E and 2F could be produced and used in a scale of or around 1:1. FIG. 2A also shows a screw of the screw device with a screw bolt 20.1 and a nut, or respectively a screw cap 20-2, is also represented in FIG. 2A. In the same way as with the hook in accordance with FIG. 1, this hook 12 also has the hook element 16 and the shackle element 18. The shackle element 18 forms a groove with the groove bottom 18.1 and the two lateral walls 18.2, 18.3.

As can best be seen in FIG. 2A, the groove bottom 18.1 is embodied in such a way, that it surrounds the fixation rod, no longer represented in FIGS. 2B to 2F, in the circumferential direction of the rod, by more than 180°, namely by 180° plus an additional small angle α, more precisely by 180+α; the angle α is in the range between 0.5° and 80° and is preferably 25° to 40°. This is the case because the distance between the two lateral walls 18.2, 18.3 is slightly less than the diameter of the circle, which can be drawn in the groove bottom 18.1, or respectively that of the fixation rod 10. It is therefore necessary to spread the lateral walls 18.2, 18.3 slightly apart from each other, so that they form a small angle β, for introducing the fixation rod 10. FIG. 2D shows the contour of the groove 18 in dash-dotted line before and in full line after spreading apart the lateral walls 18.2, 18.3.

It is of course possible to perform an elastic or plastic deformation to spread apart the lateral walls 18.2, 18.3 just before the fixation rod 10 is introduced. But it is more convenient and highly preferred to perform a plastic deformation to spread apart the lateral walls 18.2, 18.3 before, e.g. while the hook is manufactured.

When making the shackle element of the hook 12, usually a bore with a diameter lesser than the diameter of the fixation rod 10 is drilled in a piece of a suitable material. The bore is then worked so that it's surface is perfectly even. The bore defines the groove bottom 18.1. To obtain the two lateral walls 19.2, 18.3 of the groove, a slit is cut by a milling operation, extending along a plane containing the longitudinal axis of the bore. As can be seen in FIG. 2B, the surfaces of the lateral walls 18.2, 18.3 which face each other are now in parallel alignment, and the distance between these parallel surfaces is determined by the width of the slit. This distance between the lateral walls 18.2, 18.3 is lesser then the diameter of the fixation rod 10 and therefore is not large enough to for an opening for introducing the fixation rod. Now the two lateral walls 18.2, 18.3 are spread apart, so that they are no longer parallel but form the small angle β, as shown in FIGS. 2C and 2D. The angle β is determined by the diameter of the fixation rod 10, or, more exactly, by the difference between the diameters of the fixation rod 10 and the bore, and also by the width of the slit between the parallel lateral walls 18.2, 18.3, or by the angle α. Now the shackle element has an opening which is sufficiently large for the fixation rod 10.

Before machining the slit which separates the lateral walls 18.2, 18.3, circumferential or almost circumferential rills 19 can be machined along the surface of the bore; these rims are depicted in FIGS. 2E and 2F. The rills 19 eliminate or diminish the friction between the friction rod 10 and the shackle element of the hook.

As can best be seen in FIG. 2F, a through bore 22 has been cut into the lateral wall 18.2, and a bore, or respectively an interior screw thread 24, in the lateral wall 18.3. In order to obtain a sufficient length of the screw thread, the lateral wall 18.3 is made thicker in the direction of the axis 14 than the lateral wall 18.2. Preferably the diameter of the bore 22 in the lateral wall 18.2 is slightly larger than the diameter of the bore in the lateral wall 18.3.

When tightening the screw 20.1, 20.2 after introducing the fixation rod 10, an elastic and possibly also a plastic deformation of the two lateral walls 18.2, 18.2, in particular of the thinner lateral wall 18.2, takes place, whereby essentially the angle between the lateral walls 18.2, 18.3 becomes smaller than the angle β.

FIG. 2A shows that the distance of the axis 14 of the screw device from the center of the circle, which can be drawn in the groove bottom 18.1, or respectively from the longitudinal axis 11 of the fixation rod 10, and the diameter of the screw bolt 20.1 are of such size that in the assembled state the screw bolt 20.1 and the fixation rod 10 touch.

The surface of the lateral wall 18.2 facing the shackle element—or respectively the rear in case of the patient—has a protrusion 26, which is elastically deformed in the course of tightening the screw by means of the nut 20.2, and in this way forms a securing device for the screw.

A cutout 28 is used for grasping the hook with suitable pliers. The cutout 28 and/or further cutouts for the same purpose can also be arranged at other locations of the hook 12.

FIGS. 3A and 3B represent a rod connector 32, which is used for the connection with each other of the essentially vertical fixation rod 10 and an at least approximately horizontal transverse rod 10.1, as can be seen in FIG. 6. The rod connector 32 has a clamping device 34 for the transverse rod 10.1 and the shackle element 18 for clamping the fixation rod 10, which is essentially designed in the same way as the shackle element described in connection with the hooks of FIGS. 2A to 2F.

Figures 4A, 4B:
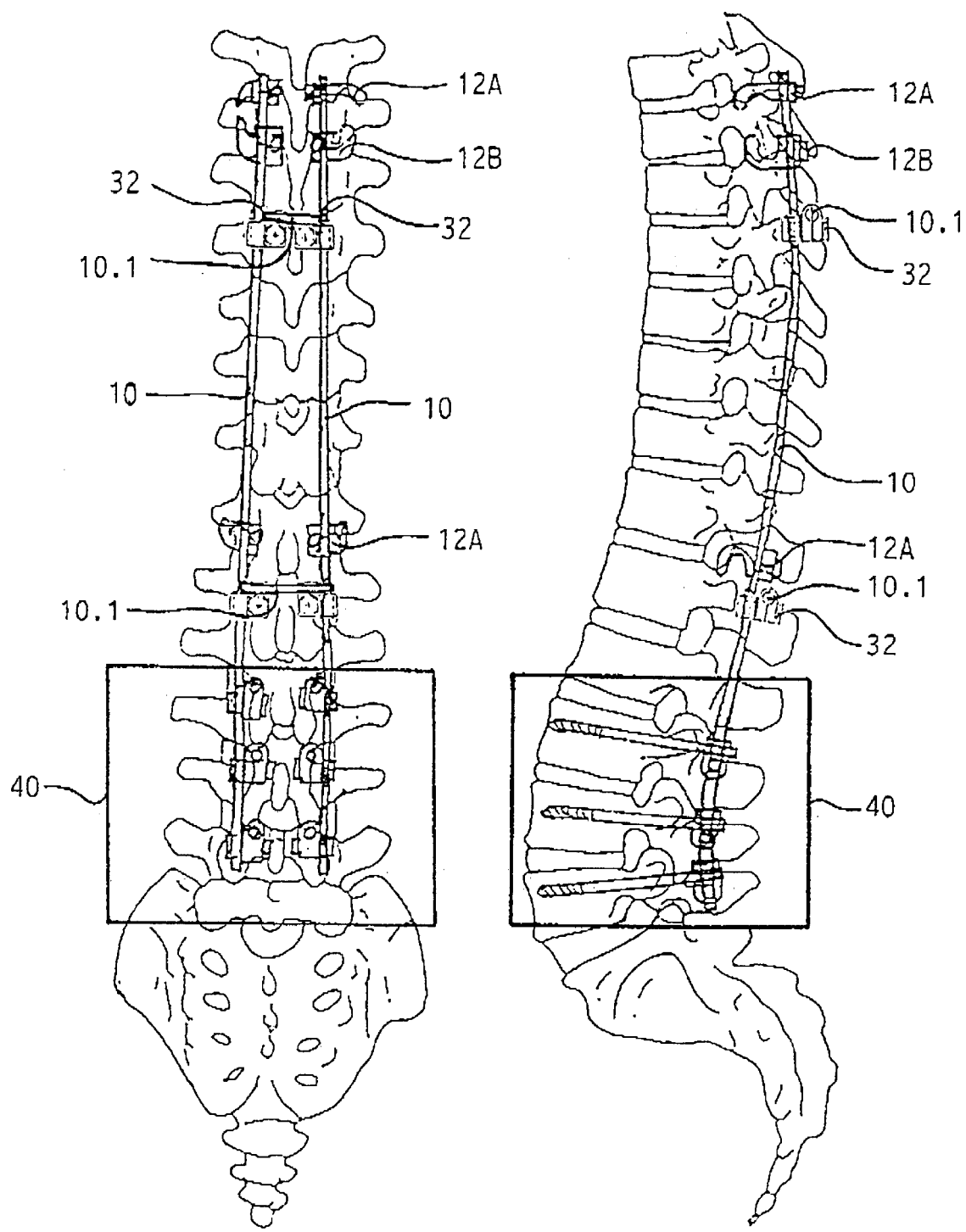
FIG. 4A represents a section of a spine with an internal fixation device of two fixation rods and several hooks in a view from behind.
FIG. 4B represents the section of a spine represented in 5A with an internal fixation device in a view from the side.

A section of the spine of the patient with an internal fixation device is represented in FIGS. 4A and 4B. It consists of two fixation rods 10, each of which is equipped with several hooks 12 gripping from above and below. As is customary, transverse rods 10.1 extend between the two fixation rods 10, wherein the fixation rods 10 and the transverse rods 10.1 are fastened to each other by means of rod connectors 32. The hooks, and in particular the hook elements are designed as a function of their use, for example as pedicle, lamina, lumbar or transversal hooks. Pedicle hooks are identified with 12A and transversal hooks with 12B in FIGS. 4A and 4B. The area in which the anchoring of the fixation device, for example by means of pedicle screws, takes place, is identified by 40.

Figure 5:
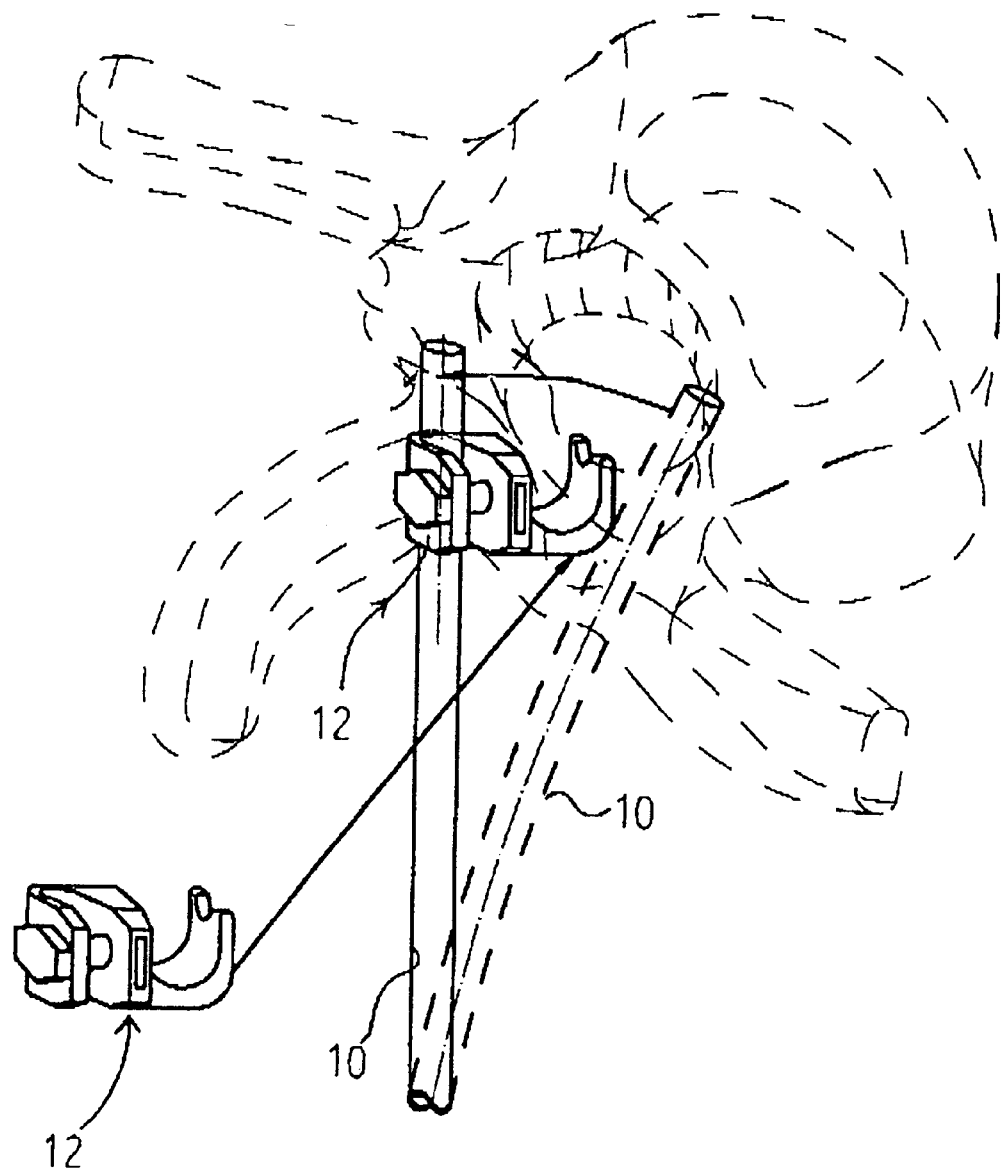
FIG. 5 represents implanting of a hook and fixation rod.

FIG. 5 is self-explaining and shows the benefit of the hook in accordance with the invention when implanting the fixation device. Hook 12 is shown twice, below alone before being implanted, and also after being implanted. When implanting the whole device, first the hook 12 and other hooks, not shown, are implanted. Due to the spread apart lateral walls 18.2, 18.3 the fixation rod 10, which is depicted in dashed lines before and in normal lines after introduction, can then be introduced transversely between the lateral walls 18.2, 18.3 into the groove 18.1. Hence it is therefore possible to implant several hooks and to introduce afterwards the fixation rod 10 transversely. This is much more convenient than introducing the fixation rod 10 longitudinally by sliding it in the direction of it's axis to pass it through the different hooks, or by implanting the hooks with the fixation rod already introduced. Still the rod will be perfectly fixed within the shackle Hooks, screws, fixation rods, transverse rods and all further implant components are made of the same material, preferably of a suitable chromium steel or titanium-niobium alloy or a suitable plastic material. It is important that the materials used for the implants are bio-compatibel but in now case biodegradable. It is highly recommended to use materials which do not result in an electric element. It is further important to use materials that can be manufactured and stored without the need of using products like lubricants or conserving products which are difficult to be wash of before implanting takes place.

Preferred types of fixation rods 10 have diameters of 4.5 mm, 5 mm, 5.5 mm, 6 mm, 6.5 mm or 7 mm. The diameter of the machined bore is preferably between 0 and 0.05 mm larger than the diameter of the fixation rod. The width of the slit is preferably 0.1 to 0.5 mm lesser than the diameter of the bore. The wall thickness is between 1 mm and 3 mm, preferably about 1.5 mm. The height is between 5 mm and 20 mm, preferably between 6.5 mm and 13 mm. A suitable screw is screw with a thread M4×0.5; in any case the thread must be a fine thread. To fix the screw it will be necessary to apply between 5 Nm and 10 Nm.

A multitude of further embodiments are possible within the scope of the invention besides the hooks, or respectively rod connectors, represented in FIGS. 1 to 5 and described above.

What is claimed is:

1. A shackle element adapted to clamp a fixation rod essentially extending along a spine, having
    a groove with a groove bottom extending in cross section along an arc of 180° plus a partial angle in a range between 0.5° and 80°, being intended for a longitudinally displaceable reception of the fixation rod restable on the groove bottom so that the fixation rod is enclosable by more than 180° in a circumferential direction thereof,
    two lateral walls adjoining the groove bottom, the lateral walls formed at an angle to each other with a distance between the lateral walls increasing with a growing distance from the groove bottom in order to form an entrance wide enough to introduce the fixation rod into the groove, a first one of the lateral walls being thinner than a second one of the lateral walls which is thicker than the first one of the lateral walls, a hook element of a hook protruding from the thicker wall, and
    a screw device for clamping the fixation rod, being designed and arranged in such a way that the lateral walls of the shackle element can be pressed toward each other after introducing the fixation rod for clamping the fixation rod.

2. The shackle element in accordance with claim 1, wherein the screw device comprises an interior screw thread in one of the lateral walls and an outer screw thread on a screw bolt, which can be screwed into the interior screw thread through an unthreaded through bore in the other lateral wall.

3. The shackle element in accordance with claim 2, wherein the lateral wall provided with the interior screw thread has been made thicker in the direction of the axis of the screw device than the lateral wall provided with the unthreaded through bore.

4. The shackle element in accordance with claim 2, wherein an exterior surface of the lateral wall provided with the unthreaded through bore, has at least one protrusion which can be elastically deformed by means of a nut or a screw cap of the screw device in order to form a securing device for the screw.

5. The shackle element in accordance with claim 1, wherein the groove bottom has circumferential or almost circumferential rills.

6. A method of making the shackle element for clamping a fixation rod of claim 1, the shackle element having a groove with a groove bottom extending in cross section along an arc of 180° plus a partial angle in a range between 0.5° and 80°, two lateral walls adjoining the groove bottom, the method comprising the steps of:
    forming a bore with a bore axle, the bore having a diameter at least equal to the diameter of the fixation rod,
    forming a slit along a plane comprising the bore axle, hereby forming the two lateral walls, the width of the slit being lesser than the diameter of the fixation bar, and
    spreading apart from each other the lateral walls, so that they form an angle and the distance between the walls increases with growing distance from the groove in order to form an entrance for introducing the fixation rod.

7. The shackle element in accordance with claim 1, wherein the partial angle is between 25° to 40°.

8. The method in accordance with claim 6, wherein the partial angle is between 25° to 40°.

9. The shackle element in accordance with claim 1, wherein the surface of the groove bottom is smooth.

10. The method in accordance with claim 6, wherein the surface of the groove bottom is smooth.

* * * * *